US00PP33994P2

(12) United States Plant Patent
Doll

(10) Patent No.: US PP33,994 P2
(45) Date of Patent: Mar. 1, 2022

(54) ***SEDUM* PLANT NAMED 'DOLSEB'**

(50) Latin Name: ***Sedum* hybrid**
Varietal Denomination: Dolseb

(71) Applicant: Marie-France Doll, La Foret Fouesnant (FR)

(72) Inventor: Marie-France Doll, La Foret Fouesnant (FR)

( * ) Notice: Subject to any disclaimer, the term of this patent is extended or adjusted under 35 U.S.C. 154(b) by 0 days.

(21) Appl. No.: 17/407,088

(22) Filed: Aug. 19, 2021

(51) Int. Cl.
*A01H 5/00* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Sedum* plant named 'Dolseb' that is characterized by its upright, strong stems with suitability for use in large containers, its narrow leaves, its dark burgundy foliage, its well-branched growth habit, its resistance to mildew, its flowers that are red-pink in color and bloom in August to October in France, and its plant height of 40 cm.

2 Drawing Sheets

Botanical classification: *Sedum* hybrid.
Variety denomination: 'Dolseb'.

CROSS REFERENCE TO A RELATED APPLICATION

This application is related to a European plant breeders' rights application filed on Dec. 10, 2019, application No. 2019/3358. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Sedum* plant, botanically of hybrid origin and known as *Sedum* 'Dolseb' referred to hereinafter by its cultivar name, 'Dolseb'. The new cultivar of *Sedum* is a hardy herbaceous perennial grown for use as a landscape and container plant.

'Dolseb' was discovered by the Inventor as a chance seedling in a trial field planted with *Sedum* in La Foret Fouesnant, France in 2015. The parentage is unknown.

Asexual propagation of the new cultivar was first accomplished by stem cuttings by the Inventor in 2015 in La Foret Fouesnant, France. Asexual propagation by stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Dolseb' as a unique cultivar of *Sedum*.

1. 'Dolseb' exhibits upright, strong stems; suitable for use in large containers.
2. 'Dolseb' exhibits narrow leaves.

3. 'Dolseb' exhibits dark burgundy foliage.
4. 'Dolseb' exhibits a well-branched growth habit.
5. 'Dolseb' exhibits resistance to mildew.
6. 'Dolseb' exhibits flowers that are red-pink in color and bloom in August to October in France.
7. 'Dolseb' exhibits a plant height of 40 cm.

'Dolseb' can be compared to *Sedum* cultivars 'Night Embers', (U.S. Plant Pat. No. 29,211), 'Dark Magic' (U.S. Plant Pat. No. 27,619), and 'Touchdown Teak' (U.S. Plant Pat. No. 26,078). All are similar to 'Dolseb' in having dark colored foliage. 'Night Embers' differs from 'Dolseb' in having foliage that is wider, slightly less dark foliage, larger inflorescences, and a greater plant size. 'Dark Magic' differs from 'Dolseb' in having shorter stem internodes and larger inflorescences that are more purple in color. 'Touchdown Teak' differs from 'Dolseb' in having larger inflorescences that are darker in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by perennials.com, planttipp.eu, thichdalat.vn, qualitycuttings.com, gardentags.com, terranovanurseries.com, garden.org, pinterest.com, procvetok.com, rhs.org.uk, plants.spruceitupgardencentre.com. nova.co.at, florapont.hu, en.floraplanet.com, gardenhaven.co.uk, plantsshootsandleaves.co.uk, daugiametes.lt, sklep.barcikowscy.eu.

BRIEF DESCRIPTION OF THE DRAWINGS

The accompanying color photographs illustrate the overall appearance and distinct characteristics of the new *Sedum*.

The photographs were taken of a plant about 2 years in age as grown in a garden in Geldermalsen, The Netherlands.

Figure 1:
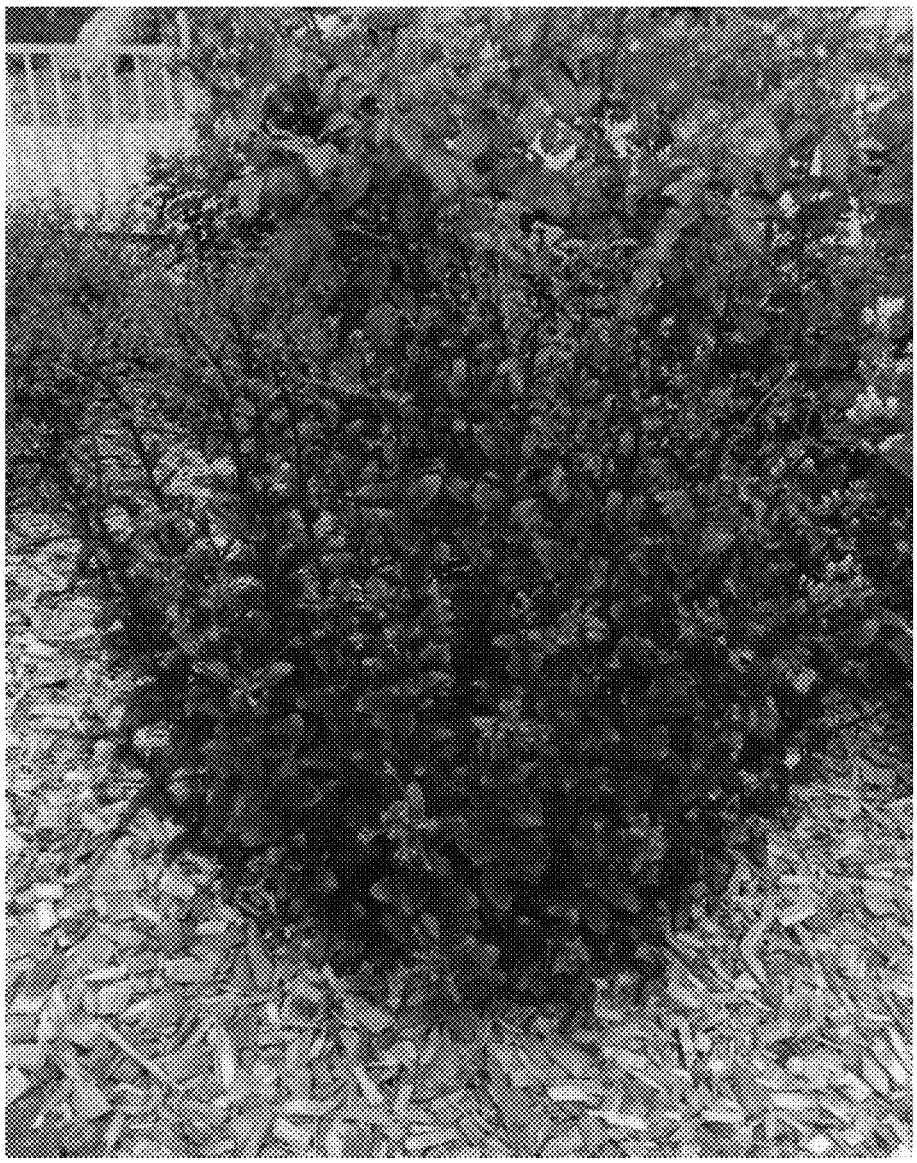

The photograph in FIG. 1 provides a view of the plant habit and foliage coloration of 'Dolseb' in summer.

Figure 2:
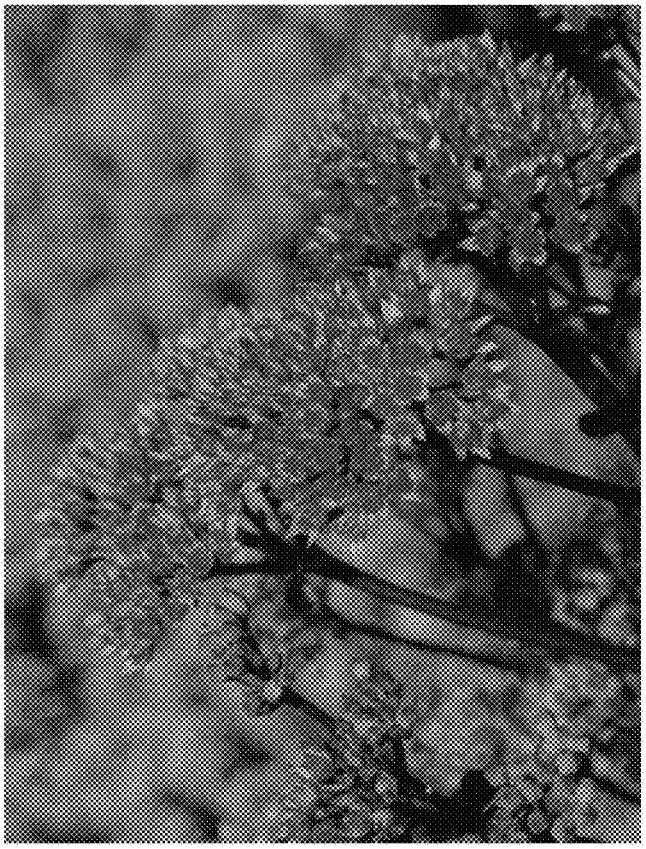

The photograph in FIG. 2 provides a view of the inflorescences of 'Dolseb' in June.

Figure 3:
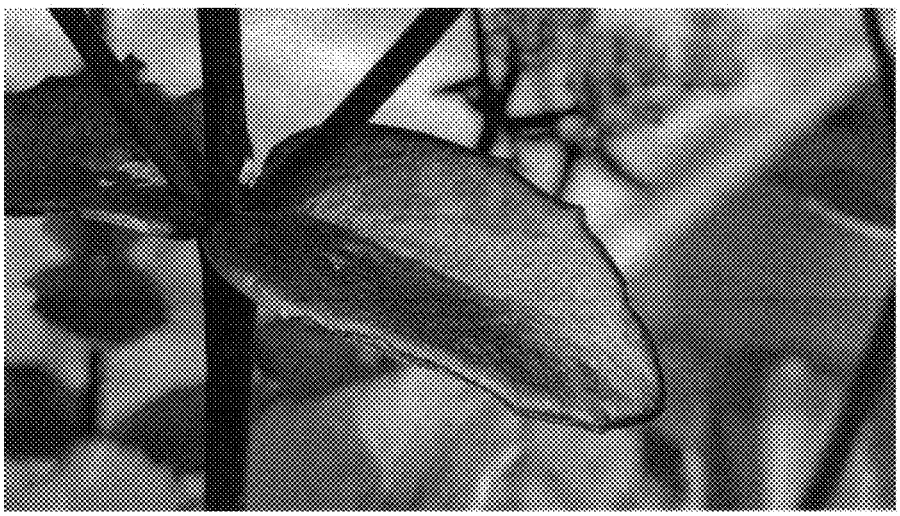

The photograph in FIG. 3 provides a view of the upper surface of a leaf of 'Dolseb'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 2-year-old plants of 'Dolseb' as field grown in 17-cm containers in Geldermalsen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—August to October in France.
*Plant type*.—Herbaceous perennial.
*Plant habit*.—Upright, well-branched, strong stems.
*Height and spread*.—Average of 40 cm in height and about 50 cm in spread as a 2-year-old plant in the landscape.
*Hardiness*.—At least hardy in U.S.D.A. Zones 5 to 9.
*Disease and pests*.—Resistance to powdery mildew has been shown (typically caused by *Erysiphe sedi, Eysiphe umbilici* or *Golvinomyces orontii*).
*Root description*.—Fibrous, 155A.
*Propagation*.—Stem cuttings.
*Growth rate*.—Moderately vigorous.
*Rooting*.—Roots initiate in about 2 weeks, a young plant can be produced in a about 6 weeks in spring and summer.

Stem description:

*Stem shape*.—Rounded.
*Stem size*.—An average of 23 cm in length and 5 mm in width.
*Internode length*.—Average of 4 cm.
*Stem color*.—Young and mature main branches; 187A, suffused with 183A, young and mature lateral branches; 187A.
*Stem surface*.—Slightly glossy.
*Branching habit*.—Average angle of 75°, strong, average of 3 main branches, an average of 3 branches per main branch.

Foliage description:

*Leaf shape*.—Ovate, elliptical.
*Leaf division*.—Simple.
*Leaf arrangement*.—Alternate.
*Leaf base*.—Truncate.
*Leaf apex*.—Rounded.
*Leaf venation*.—Pinnate, color of midrib upper surface N186A, color of midrib lower surface 183A, secondary veins not visible.
*Leaf margins*.—Irregularly and bluntly dentate.
*Leaf attachment*.—Sessile.
*Leaf orientation*.—Outward.
*Leaf texture*.—Thick, succulent.
*Leaf surface*.—Both surfaces are smooth and glabrous.
*Leaf color*.—Young and mature upper surface; closest to N186A, margins and base 183A, young and mature lower surface; 137C, margins and base suffused with 183A.
*Leaf size*.—Average of 5.2 cm in length, 3.3 cm in width, and 1 mm in width.

Flower description:

*Inflorescence type*.—Compound cyme.
*Inflorescence size*.—An average of 8 cm in diameter and height.
*Lastingness of inflorescence*.—At least one month.
*Flower type*.—Perfect, spreading, 5-starred.
*Flower number*.—An average of 600 flowers per plant.
*Flower fragrance*.—None.
*Flower buds*.—Lanceolate in shape, 3 mm length and 3.5 mm in width, glabrous surface, color; a blend of 53B, 53C, and 155B.
*Flower size*.—About 6 mm in depth and 5 mm in diameter.
*Peduncles*.—Round in shape, an average of 3.5 cm in length and 3.5 mm in diameter, surface is glabrous, strong, 183A in color.
*Pedicels*.—Round in shape, an average of 3.5 mm in length and 1 mm in diameter, surface is glabrous, strong, 183A in color.
*Calyx*.—5-parted, fused at base, 1.5 mm in length, 2.5 mm in width.
*Sepals*.—5, average of 1.5 mm in length, 1 mm in width, campanulate in shape, entire margin, acute apex, fused base, both surfaces glabrous, both surfaces 137B in color and suffused with 183A.
*Petals*.—5, spreading, 4 mm in length and 2 mm in width, lanceolate in shape, fused base, acute apex, entire margin, color; upper and lower surface when opening and fully open; base 155B, center and top 53C.

Reproductive organs:

*Pistils*.—5, showy, 4 mm in length 1 cm in diameter, stigma; minute, N155C in color, style; ovate, rounded in shape, cone like, and N74A in color, ovary; small, single celled and translucent in color.
*Stamens*.—10, about 3 mm in length, 2 mm in diameter, filament; very fine, NN155D in color, anther; club shaped, 0.7 mm in length, 0.6 mm in width, N74A in color, pollen was not observed.
*Fruit*.—Fruit and seed production has not been observed to date.

It is claimed:

1. A new and distinct variety of *Sedum* plant named 'Dolseb' as described and illustrated herein.

* * * * *